United States Patent
Gale et al.

[11] Patent Number: 5,885,342
[45] Date of Patent: Mar. 23, 1999

[54] BLENDED NACREOUS PIGMENTS, COLORANTS AND ADJUVANTS

[75] Inventors: Jeannine M. Gale, Peekskill; Betty F. Aucar, Ossining; James D. Christie, Tuckahoe, all of N.Y.

[73] Assignee: Engelhard Corporation, Iselin, N.J.

[21] Appl. No.: 853,928

[22] Filed: May 9, 1997

[51] Int. Cl.⁶ .................................................. C09B 63/00
[52] U.S. Cl. ..................... 106/417; 106/402; 106/415; 106/418
[58] Field of Search ................... 106/402, 415, 106/417, 418

[56] References Cited

U.S. PATENT DOCUMENTS

| | | | |
|---|---|---|---|
| 3,647,492 | 3/1972 | Chapman et al. | 106/417 |
| 3,656,982 | 4/1972 | Chapman et al. | 106/417 |
| 4,084,983 | 4/1978 | Bernhard et al. | 106/402 |
| 4,323,554 | 4/1982 | Bernhard . | |
| 4,328,146 | 5/1982 | Andy | 106/417 |
| 4,968,351 | 11/1990 | Ahmed et al. | 106/402 |
| 5,074,917 | 12/1991 | Persello | 106/402 |
| 5,336,306 | 8/1994 | Hughes et al. | 106/31.1 |
| 5,336,309 | 8/1994 | Noguchi et al. | 106/417 |

FOREIGN PATENT DOCUMENTS

| | | |
|---|---|---|
| 0220617 A2 | 5/1987 | European Pat. Off. . |
| 0554776 A1 | 8/1993 | European Pat. Off. . |

OTHER PUBLICATIONS

Database WPI Week 9227; Derwent Publications Ltd. AN 92–223554; JP 04 149 277 A (KAO); May 22, 1992; Abstract.

Database WPI Week 7804; Derwent Publications Ltd. AN 78–07550A; JP 52 148 632 A (Pola Kasei Kogyo K.K.); Dec. 10,1997; Abstract.

Perry's Chemical Engineers'Handbook, 6th Ed., Mcgraw–Hill, NY, pp. 8/60, 8/61 and 8/65–8/68. Dec. 1984.

*Primary Examiner*—Mark L. Bell
*Assistant Examiner*—Scott L. Hertzog
*Attorney, Agent, or Firm*—Ostrolenk, Faber, Gerb & Soffen, LLP

[57] ABSTRACT

Colored lustrous pigments of superior quality are prepared by dry blending a metal oxide-coated mica nacreous pigment and a colorant lake with a blend adjuvant. The resulting blend exhibits a well dispersed, stable coloration, increased hydrophobicity and is particularly useful in cosmetic applications.

22 Claims, No Drawings

BLENDED NACREOUS PIGMENTS, COLORANTS AND ADJUVANTS

BACKGROUND OF THE INVENTION

Colored lustrous pigments are known in which the colorant is selected from a wide variety of inorganic and organic coloring agents or dyestuffs and the lustrous pigment is a natural pearlescent material or synthetic pearlescent substance (also called nacreous pigments). Numerous difficulties were encountered in the prior art when making such colored lustrous pigments. For example, severe bleeding of the color on filtration of the coated product from the suspension, poor adherence of the dyestuff on the surface of the pigment such that the color could be washed off with water, difficulty in retaining luster with increased color intensity, and non-uniform distribution of the dyestuff on the pigment surface have been noted.

The foregoing is described in part in U.S. Pat. No. 4,084,983. That pigment relates to the use of titanium dioxide coated mica pigments to produce colors due to the interference phenomenon and additional color effects are achieved by coating organic dyes on the surface of those pigments. An improvement in the process of that patent is set forth in U.S. Pat. No. 4,968,351 in which is described a process of absorbing a soluble organic dyestuff at a coating pH on the surface of the metal oxide coated substrate nacreous pigment in an aqueous dispersion and subsequently absorbing a laking reagent thereon.

As apparent from the patents just described, the selection of treatment conditions to achieve a desired product can be difficult because, for example, the respective pigments and dyes have different cohesive forces. In addition, some pigments and dyes do not have sufficient dispersion stability and reaggregation of the pigment particles occurs and good coloration is not achieved.

A different approach is described in U.S. Pat. No. 5,336,309. In that patent, the platy substrate and dye are subjected to high speed stirring for a predetermined period of time in the absence of a liquid medium, for the purpose of coating the surfaces of the platy pigment with the dye by forming an "ordered mixture". This method of achieving colored lustrous pigments by high speed dry stirring or blending requires that the stirring energy imparted to the mixture be critically adapted into the components being blended. For example, Example 3 and Comparative Example 2 of the patent combined the same titanium oxide-coated mica with the same organic pigment. When the stirring energy was 84.2 kJ and the stirring speed of 70 m/sec was employed, a colored pigment with dispersibility was achieved. However, when the energy was 20.7 kJ and the stirring speed of 20 m/sec was employed, the resulting product was found to contain aggregates of the organic pigment particles.

It has now been discovered that the dry blending process can be improved if certain selected adjuvants are also employed. The resulting product has increased hydrophobicity and requires a lower amount of energy to be used in the blending step. The process improves the adherence and distribution of the dye on the pearlescent pigment and the resulting product is a stable dispersion, particularly suitable for use in cosmetic applications. The selected adjuvant eases the blending process, improves the quality and stability of the colorant dispersion and is a "value added" component of the final product.

It is therefore the object of the present invention to provide a new colored lustrous pearlescent pigment and a method by which such pigment can be manufactured. This and other objects of the invention will become apparent to those skilled in the art from the following detailed description.

SUMMARY OF THE INVENTION

The present invention relates to colored lustrous pigments of superior quality and to the process of producing them. More particularly, the invention relates to a colored lustrous pigment comprising platy substrate such as a metal oxide-coated mica nacreous pigment, colorant lake and adjuvant in which the pigment exhibits a contact angle of water greater than 90°. The pigment is realized by blending the metal oxide-coated mica, colorant lake and at least one adjuvant selected from natural and synthetic oils, hydrolyzed proteins, fatty acids, fatty acid esters, fatty acid-amino acid peptide dimers, p-hydroxybenzoic acid esters and phenoxy alcohols.

DETAILED DESCRIPTION OF THE INVENTION

In accordance with the present invention, an improved colored lustrous pigment is achieved by dry blending a platy substrate such as a metal oxide-coated mica nacreous pigment with a colorant lake and a selected adjuvant. The blending process can be carried out in a single step in which all three ingredients are combined or sequentially in which two of the materials to be blended are first combined and blended and then the third material is added and blended. In the preferred procedure in accordance with the present invention, a metal oxide-coated pigment is first combined and blended with the colorant lake and then the adjuvant is added and blending is continued.

The substrate can be any platy material such as mica flakes, sericite, kaolin, gypsum, bismuth oxychloride and the like. Suitable mixtures of platy substrates may also be used. Preferred are the well-known metal-oxide coated mica nacreous or pearlescent pigments. They are exemplified by titanium dioxide-, zirconium dioxide- and/or iron oxide-coated mica. These pigments are described, inter alia, in U.S. Pat. Nos. 3,437,515, 3,418,146, 3,087,828 and 4,038,099. The preferred pigment is titanium dioxide-coated mica. The mica flake substrates generally have a length of about 1 to 75 microns, preferably about 5 to 35 microns, a thickness between about 0.03 and 3 microns and a specific surface area (BET) of about 1 to 10 $m^2/g$, preferably about 2 to 6 $m^2/g$. Usually, the titanium dioxide or other metal oxide is coated on the substrate surface to a thickness of about 20–350 nm. Depending on the thickness of the metal oxide coating, the pigments can exhibit interference or reflection colors of blue, green, yellow, red, etc. Any of the previously-known metal oxide-coated mica nacreous pigments can be employed in the present invention.

A colorant lake is a metal salt of a water-soluble dye extended on a substratum of metal oxide. In most instances, the metal is aluminum but it can also be, for instance, zirconium, calcium, barium or strontium. Since a principal use of the pigments of the present invention is in cosmetics, the dyes employed should be acceptable for such use. In the United States, such dyes are usually denoted by the nomenclature D&C or FD&C followed by the designated color and a number. The lake FD&C and D&C pigments are certified in the United States by the Division of Color Technology of the Food and Drug Administration of the Department of Health and Human Services. The specifications of these lake pigments are set forth in the Code of Federal Regulations, Title 21, Part 82, Subpart B, Section 82.51. An illustrative list of usable materials including the chemical identity and structure of the dye are set forth in the aforementioned U.S. Pat. No. 4,968,351, the disclosure of which is hereby incorporated by reference. Non-cosmetic colorants such as the phthalocyanines, quinacridones, perylenes, anthroquinones, and the like can also be employed to produce pigments for use in non-cosmetic applications. Mixtures of suitable colorants may also be used. In general, the dye content of the colorant lake can be about 1 to 25% by weight and is more preferably about 2 to 10% by weight, and most preferably about 2.5 to 5% by weight. In general, it will constitute about 1 to 10% of the colorant lake-pearlescent pigment combination and preferably about 1 to 5% by weight.

The adjuvant employed in the present invention is a natural or synthetic oil, hydrolyzed protein, fatty acid, fatty acid ester, fatty acid-amino acid peptide dimer, p-hydroxybenzoic acid ester or phenoxy alcohol. Examples include phenyl trimethicone, hydrogenated soybean oil, hydrogenated polyisobutene, lauroyl lysine, methyl paraben, propyl paraben, butyl paraben, palmitic acid, stearic acid, caprylic/capric triglyceride, octyldodecyl stearoyl stearate, hydrolyzed oat protein, octyl palmitate or isopropyl isostearate. These adjuvants can be used alone or in various combinations. In general, the amount of adjuvant will by about 1 to 10% based on the total weight of the three components, namely the pearlescent pigment, colorant lake and adjuvant. Preferably, the amount of adjuvant will be about 4 to 8%. Of these adjuvants, it is preferred to employ palmitic acid, hydrogenated polyisobutene and the parabens.

The three components can be combined in any order and in a single blending step or in a series of sequential blending steps. It has been found that best results are generally achieved when the pearlescent pigment and the colorant lake are first combined and blended and thereafter the adjuvant is added and blended with the combination.

The blending time, temperature and stirring speeds which combine to achieve best results are dependent on the particular identity of each of the three ingredients and the concentrations of each which are being employed. For instance, a blending time of 2 minutes may be adequate in some circumstances but inadequate in others. In most instances, ambient temperature is sufficient. Appropriate values for these parameters can be easily and quickly established by conducting a few preliminary procedures. In general, stirring speeds equivalent to those provided by the commercially-available PK, Osterizer and Waring blenders can be employed. The blending time can vary from a few seconds to several hours but is preferably about 1 to 30 minutes, most preferably about 2 to 7 minutes, in an Osterizer or Waring blender.

In some instances it has been found preferable to dry the blend at an elevated temperature of about 50° to 125° C. and more preferably about 60°–90° C. for about 0.25–5 hours, preferably about 1–3 hours.

The resulting lustrous colored nacreous pigment has increased hydrophobicity. A convenient method of establishing the hydrophobicity is by measuring the contact angle of water with the resulting pigment. Surfaces exhibiting convex angles of water greater than about 90° are said to be hydrophobic. The procedure for carrying out this measurement is well-known. In general, the contact angle of water for the products of the present invention will be at least 90° and most preferably in excess of about 100°.

In order to further illustrate the present invention, various examples are set forth below. In these examples, as throughout this specification and claims, all temperatures are in degrees centigrade and all parts and percentages are by weight unless otherwise indicated.

In Examples 1–21, hydrophobicity was assessed by sprinkling about 1 gram of the pigment onto the surface of a one ounce jar filled with two-thirds ounce of distilled water. A number between 0 and 5 was assigned to differentiate the degree of hydrophobicity with 0 being hydrophilic and 5 being hydrophobic. In addition, the colorant attachment was assessed by using a 1,000× optical microscope and visually rating the product upon a numerical scale of 0 to 5. A value of 0 indicates no evidence of attachment, 1 indicates slight attachment, 2 indicates some attachment, 3 indicates moderate attachment, 4 indicates most color particles on the pigment, and 5 indicates all the colorant particles on the pearlescent pigment surface.

The contact angle of water in Examples 37 et seq. were calculated using a modification of the Wilhelmy Plate procedure described in the article by Shanker et al., "Development of a New Technique for the Assessment of Wettability of Powders", J. Pharm. Res., 11, 5243 (1994). The powder tested is adsorbed onto a one inch square slip of double sided adhesive tape which is then suspended from a microbalance and a force-depth isotherm is recorded as the slip is immersed in water. The force measured is extrapolated to the point of zero immersion where the buoyancy is zero. At this point, $\cos \theta = mg/\sigma P$, where m is the mass measured by the balance, g is the gravitational acceleration constant, $\sigma$ is the surface tension of water, P is the perimeter of the slip and $\theta$ is the contact angle of water with the sample.

In the following examples, the procedure employed involved blending the pearlescent pigment and the colorant for 3×1 minute in an Osterizer blender and then adding the wetting agent and blending for an additional 2×1 minute.

EXAMPLES 1–3

A commercially available gold colored titanium dioxide-coated mica was blended with FD&C Yellow #5 aluminum lake. When 90 parts of the pearlescent pigment was blended with 10 parts of the lake, the hydrophobicity was 0 and the attachment 3. The procedure was repeated replacing 7.5 parts of the pearlescent pigment with hydrogenated soybean oil which caused the hydrophobicity to increase to 3 and the attachment to increase to 5. Repeating the experiment employing phenyl trimethicone as a replacement for the soybean oil resulted in a hydrophobicity of 3 and an attachment of 5.

EXAMPLES 4–5

Dry blending was carried out employing 61.9 parts of a commercially available gold colored titanium dioxide-coated mica, 20.0 parts mica, 0.6 parts lauroyl lysine, 7.5 parts hydrogenated soybean oil and 10 parts of FD&C Yellow #5 aluminum lake. The hydrophobicity was 4 and the attachment was 3. Repeating this procedure using 77.5 parts of the pearlescent pigment, 5 parts of mica, 7.5 parts of phenyl trimethicone and 10 parts of the aluminum lake resulted in a dry blended product in which both the hydrophobicity and attachment were 4.

EXAMPLE 6

The dry blending procedure was repeated employing 45.0 parts of the gold colored titanium dioxide-coated mica, 43.5 parts of mica, 1.4 parts of lauroyl lysine and 10 parts of FD&C Yellow #5 aluminum lake. This resulted in a hydrophobicity of 5 and an attachment of 3.

EXAMPLE 7

72.1 parts of a green colored commercially available titanium dioxide-coated mica was blended with 4.85 parts of mica, 0.15 parts lauroyl lysine, 2.3 parts of FD&C Yellow #5 aluminum lake (27% dye), 15.6 parts of FD&C blue #1 aluminum lake (12% dye) and 5 parts of phenyl trimethicone. The hydrophobicity was 5 and the attachment 2.

EXAMPLE 8

71.5 parts of a gold colored commercially available titanium dioxide-coated mica was blended with 5 parts of mica, 18.5 parts of FD&C Yellow #5 aluminum lake (27% dye) and 5 parts of oat protein (2% solution in distilled water). The hydrophobicity was 5 and the attachment 4.

EXAMPLES 9–10

76.48 parts of a gold colored titanium dioxide-coated mica, 18.52 parts of FD&C yellow #5 aluminum lake (27% dye) and 5 parts of octyl palmitate were combined. At the conclusion of the blending process, the hydrophobicity was 0 and the attachment 4. When the blend was dried at 90° C. for 2 hours, the hydrophobicity was 5 and the attachment 4.

EXAMPLES 11–13

Blended together were 74.2 parts of a blue commercially available titanium dioxide-coated mica, 20.8 parts of FD&C blue #1 aluminum lake (12% dye) and 5 parts of octyl palmitate. The hydrophobicity was 0 and after drying at 80° C. for either 2 or 17 hours, the hydrophobicity was 5. In each case, the attachment was 2.

EXAMPLES 14–16

Blended together were 81.8 parts of a red colored commercially available titanium dioxide-coated mica, 13.2 parts of FD&C Red #40 lake aluminum (38% dye) and 5 parts of octyl palmitate. The hydrophobicity was 0 and after drying at 90° C. for either 2 or 17 hours, the hydrophobicity was 5. In all three cases, the attachment was rated as 4.

EXAMPLES 17–19

A commercially available green colored titanium dioxide-coated mica in an amount of 64.9 parts was blended with 9.3 parts of FD&C Yellow #5 aluminum lake (27% pigment), 20.8 parts FD&C blue #1 lake (12% dye) and 5 parts of octyl palmitate. The hydrophobicity was 0 but when dried at 80° C. for either 2 or 17 hours, the hydrophobicity was rated as 5. In all three cases, the attachment was rated as 2.

EXAMPLES 20–21

Combined were 73 parts of a blue colored titanium dioxide-coated mica nacreous pigment, 20.9 parts of FD&C Blue #1 aluminum lake (12% dye) and 6 parts of isopropyl isostearate. The resulting pigment was dried at room temperature to give a product with a hydrophobicity rating of 0 and an attachment of 3. When the same pigment was dried in an oven for 2 hours at 70° C., the hydrophobicity rating increased to a value of 5.

EXAMPLES 22–24

In these experiments, the contact angle of water with the final pigment was measured. In the first procedure, 81.5% of a gold colored titanium dioxide-coated mica and 18.5 parts of FD&C Yellow #5 aluminum lake were combined. The contact angle of water of the product was 12°. The procedure was then repeated replacing 6 parts of the titanium dioxide-coated mica with octyl palmitate. The contact angle of order was found to have increased to 50°. The second experiment was repeated except that the resulting product was dried in an oven at 90° for 2 hours. The contact angle of water was then determined to be 154°.

EXAMPLES 25–27

Three products were prepared by blending 20.8% FD&C Blue #1 aluminum lake with 73.2% blue colored titanium dioxide coated mica and 6% adjuvant. The resulting products were heated in an oven at 90° C. for 2 hours. The first pigment (hereinafter designated blend A) employed octyl palmitate. The second pigment (hereinafter blend B) employed hydrolyzed oat protein. The third product employed octyl palmitate as the adjuvant but the equipment used to effect the blending was a PK blender and the temperature of the drying oven was 70° C. (blend C).

EXAMPLES 25–32

Products were formulated into lipsticks, eye shadow, cream eye shadow and lotions as shown in the following tables:

| LIPSTICK FORMULATIONS | | |
|---|---|---|
| Example | 25 | 26 |
| Lipstick Base | 40.30 | 40.30 |
| Castor Oil (q.s. to 100%) | 44.70 | 44.70 |
| BLEND A | 15.00 | -.-- |
| BLEND B | -.-- | 15.00 |
| Total | 100.00 | 100.00 |

| EYE SHADOW FORMULATIONS | | | | |
|---|---|---|---|---|
| Example | 27 | 28 | 29 | 30 |
| Talc | 34.30 | 34.30 | 38.60 | 34.30 |
| Zinc Stearate | 8.00 | 8.00 | 8.00 | 8.00 |
| Kaolin | 8.00 | 8.00 | 8.00 | 8.00 |
| Methylparaben | 0.40 | 0.40 | 0.40 | 0.40 |
| FD&C Blue #1 Lake | 9.37 | -.-- | -.-- | -.-- |
| Gold TiO$_2$-coated mica | 32.93 | -.-- | -.-- | -.-- |
| BLEND A | -.-- | 45.00 | -.-- | -.-- |
| BLEND B | -.-- | -.-- | 45.00 | 45.00 |
| Mineral Oil | 7.00 | 4.30 | -.-- | 4.30 |
| Total | 100.00 | 100.00 | 100.00 | 100.00 |

| EXAMPLE 31 CREAM EYE SHADOW FORMULATION | | |
|---|---|---|
| Phase | Ingredients | % wt. |
| I. | Water | 63.40 |
| | Magnesium Aluminum Silicate | 1.50 |
| | Methylparaben | 0.40 |
| II. | Propylene Glycol | 8.00 |
| | Cellulose Gum | 1.00 |
| III. | Triethanolamine | 0.80 |
| IV. | Stearic Acid | 3.50 |
| | Glycerol Stearate | 0.80 |
| | Oleyl Alcohol | 0.50 |
| | Propylparaben | 0.10 |
| V. | BLEND C | 20.00 |
| | Total | 100.00 |

EXAMPLE 32 LOTION FORMULATION

| Phase | Ingredients | % wt. |
|---|---|---|
| I. | Isopropyl Glycerol | 0.50 |
|  | Stearic Acid | 3.00 |
|  | Glycerol Stearate | 2.00 |
|  | Methyl Gluceth-10 | 15.00 |
|  | Propylparaben | 0.10 |
| II. | Triethanolamine | 1.00 |
|  | Water | 73.10 |
|  | Methylparaben | 0.30 |
| III. | BLEND C | 5.00 |
|  | Total | 100.00 |

EXAMPLE 33

A PK blender was loaded with 219.5 parts of blue colored $TiO_2$-coated mica and 62.5 parts of FD&C Blue #1 aluminum lake. The blender and intensifier bar were turned on and then 16.5 parts of octyl palmitate added and blended for 15 minutes. The blender was then turned off and the chamber scraped. The blender was then restarted and run for 15 minutes and then the procedure repeated until the total blend time was 60 minutes. The resulting product was spread on a glass tray and dried for 2 hours at 70° C. The product had a contact angle of water of 180°.

EXAMPLE 34

Example 33 was repeated employing a charge of 191.6 parts of a green colored $TiO_2$-coated mica, 62.5 parts of FD&C Blue #1 aluminum lake, 27.8 parts of FD&C Yellow #5 lake and 16.5 parts of octyl palmitate. The resulting product had a contact angle of water of 165°.

EXAMPLE 35

Example 33 was repeated employing 242.5 parts of a red colored $TiO_2$-coated mica, 39.5 parts of FD&C Red #40 aluminum lake and 16.5 parts of octyl palmitate. The resulting product had a contact angle of water of 152° C.

EXAMPLE 36

Example 33 was repeated employing a charge of 226.4 parts of gold colored titanium dioxide-coated mica, 55.5 parts of FD&C Yellow #5 aluminum lake and 16.5 parts of octyl palmitate. The resulting product had a contact angle of water of 138°.

EXAMPLE 37

An Osterizer was charged with 18.5 parts of FD&C Yellow #5 aluminum lake, 74.4 parts of gold colored titanium dioxide-coated mica and 0.3 parts methyl paraben and blended for 2 minutes. A mixture of 0.2 parts propyl paraben, 0.1 parts butyl paraben, 5.4 parts hydrogenated polyisobutene and 0.6 parts palmitic acid was added and blended for an additional 3 minutes. The resulting product had a hydrophobicity of 5, an attachment of 2 and a contact angle of water of 158°.

EXAMPLE 38

Example 37 was repeated employing a charge of 19.3 parts of FD&C Blue #1 aluminum lake, 74.7 parts of blue colored titanium dioxide-coated mica, 5.4 parts hydrogenated polyisobutene and 0.6 parts palmitic acid. The resulting product had a hydrophobicity of 5, an attachment of 4 and a contact angle of water of 180°.

EXAMPLE 39

Example 37 was repeated employing a charge of 20.8 parts of FD&C Blue #1 aluminum lake, 73.2 parts of blue colored titanium dioxide-coated mica, 5.5 parts hydrogenated polyisobutene and 0.5 parts stearic acid. The resulting product had a hydrophobicity of 5, an attachment of 5 and a contact angle of water of 177°.

EXAMPLE 40

Example 37 was repeated employing a charge of 20.8 parts of FD&C Blue #1 aluminum lake, 73.2 parts of blue colored titanium dioxide-coated mica, 5.5 parts octyldodecyl stearoyl stearate, and 0.5 parts stearic acid. The resulting product had a hydrophobicity of 5, an attachment of 3 and a contact angle of water of 177°.

EXAMPLE 41

Example 37 was repeated employing a charge of 20.8 parts of FD&C Blue #1 aluminum lake, 73.2 parts of blue colored titanium dioxide-coated mica, 5.5 parts caprylic/capric triglyceride and 0.5 parts stearic acid. The resulting product had a hydrophobicity of 5, an attachment of 3 and a contact angle of water of 180°.

EXAMPLE 42

Example 37 was repeated employing a charge of 20.8 parts of FD&C Blue #1 aluminum lake, 73.2 parts of blue colored titanium dioxide-coated mica, 5.5 parts caprylic/capric triglyceride and 0.5 parts palmitic acid. The resulting product had a hydrophobicity of 5, an attachment of 3 and a contact angle of water of 180°.

EXAMPLE 43

A lipstick was formulated employing 69.4 parts lipstick base, 15.6 parts castor oil and 15 parts of the blend of Example 37.

EXAMPLE 44

An eye shadow was prepared employing 141.8 parts talc, 20 parts mica, 5 parts magnesium myristate, 2 parts silica, 50 parts of the blend of Example 38, 7 parts octyl palmitate, 0.2 parts butylated hydroxytoluene and 1 part of isostearyl neopentanoate.

Various changes and modifications can be made in the process and products of the present invention without departing from the spirit and scope thereof. The various embodiments which have been set forth herein were for the purpose of further illustrating the invention but were not intended to limit it.

What is claimed is:

1. A colored lustrous pigment in the form of a free-flowing powder, which comprises a blend of platy substrate, colorant lake and an adjuvant which bonds the lake to the substrate, and which also provides the pigment with a contact angle of water of at least 90°.

2. The colored lustrous pigment of claim 1 in which the platy substrate is a metal oxide coated mica pearlescent pigment.

3. The colored pearlescent pigment of claim 2 containing at least one adjuvant selected from the group consisting of a natural oil, synthetic oil, hydrolyzed protein, fatty acid, fatty acid ester, fatty acid-amino acid peptide dimer, hydroxybenzoic acid ester and phenoxy alcohol.

4. The colored pearlescent pigment of claim 3 in which the adjuvant is selected from the group consisting of phenyl trimethicone, hydrogenated soybean oil, hydrogenated polyisobutene, methyl paraben, propyl paraben, butyl paraben, palmitic acid, stearic acid, caprylic/capric triglyceride, octyldodecyl stearoyl stearate, hydrolyzed oat protein, lauroyl lysine, octyl palmitate and isopropyl isostearate.

5. A colored pearlescent pigment free-flowing powder which comprises a blend of titanium dioxide coated mica pearlescent pigment, colorant aluminum lake and an adjuvant which bonds the lake to the substrate, and which also provides the pigment with a contact angle of water of at least about 100°.

6. The colored pigment of claim 5 in which the adjuvant is at least one member of the group consisting of palmitic acid, hydrogenated polyisobutene and paraben.

7. The colored pigment of claim 6 in which the colorant is a FD&C or D&C aluminum or calcium lake.

8. The colored pigment of claim 2 in which the colorant is a FD&C or D&C aluminum or calcium lake.

9. The colored pearlescent pigment of claim 2 in which the contact angle of water is in excess of about 100°.

10. The colored pigment of claim 1 in which the colorant is a FD&C or D&C aluminum or calcium lake.

11. The colored pearlescent pigment of claim 1 in which the contact angle of water is in excess of about 100°.

12. A method of preparing a colored pigment comprising dry blending platy substrate, colorant lake and at least one adjuvant selected from the group consisting of a natural oil, synthetic oil hydrolyzed protein, fatty acid, fatty acid ester, fatty acid-amino acid peptide dimer, p-hydroxybenzoic acid ester and phenoxy alcohol.

13. The method of claim 12 in which the platy substrate is a metal oxide coated mica pearlescent pigment.

14. The method of claim 13 in which the adjuvant is selected from the group consisting of phenyl trimethicone, hydrogenated soybean oil, hydrogenated polyisobutene, methyl paraben, propyl paraben, butyl paraben, palmitic acid, stearic acid, caprylic/capric triglyceride, octyldodecyl steroyl stearate, hydrolyzed oat protein, lauroyl lysine, octyl palmitate and isopropyl isostearate.

15. The method of claim 13 in which the metal oxide is titanium dioxide and the colorant lake is an aluminum or calcium lake.

16. The method of claim 13 in which the pearlescent pigment and colorant lake are first blended and thereafter the adjuvant is added and blended therewith.

17. The method of claim 16 in which the adjuvant is at least one member of the group consisting of palmitic acid, hydrogenated polyisobutene and paraben.

18. The method of claim 17 in which the colorant is a FD&C or D&C aluminum or calcium lake.

19. The method of claim 12 in which the metal oxide is titanium dioxide and the colorant lake is an aluminum lake.

20. The method of claim 19 in which the pearlescent pigment and colorant lake are first blended and thereafter the adjuvant is added and blended therewith.

21. The method of claim 12 in which the pearlescent pigment and colorant lake are first blended and thereafter the adjuvant is added and blended therewith.

22. The method of claim 12 in which the adjuvant is at least one member of the group consisting of palmitic acid, hydrogenated polyisobutene and paraben.

* * * * *